United States Patent
De Vries et al.

(10) Patent No.: US 10,850,990 B2
(45) Date of Patent: Dec. 1, 2020

(54) METHOD FOR PROCESSING MAGNESIUM CHLORIDE SOLUTIONS AND METHOD FOR MANUFACTURING CARBOXYLIC ACIDS

(71) Applicant: PURAC BIOCHEM BV, Gorinchem (NL)

(72) Inventors: Johannes Jeichienus De Vries, Gorinchem (NL); Raymon Frediansyah, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 104 days.

(21) Appl. No.: 16/068,989

(22) PCT Filed: Jan. 19, 2017

(86) PCT No.: PCT/EP2017/051087
§ 371 (c)(1),
(2) Date: Jul. 10, 2018

(87) PCT Pub. No.: WO2017/125496
PCT Pub. Date: Jul. 27, 2017

(65) Prior Publication Data
US 2019/0194029 A1   Jun. 27, 2019

(30) Foreign Application Priority Data
Jan. 19, 2016 (EP) .................... 16151922

(51) Int. Cl.
| | |
|---|---|
| C01F 5/00 | (2006.01) |
| C01F 5/30 | (2006.01) |
| C01B 7/03 | (2006.01) |
| C01F 5/10 | (2006.01) |
| C07C 51/02 | (2006.01) |
| B01D 1/26 | (2006.01) |
| B01D 1/28 | (2006.01) |
| C12P 7/40 | (2006.01) |
| C12P 7/42 | (2006.01) |
| C12P 7/44 | (2006.01) |
| C12P 7/46 | (2006.01) |
| C12P 7/48 | (2006.01) |
| C12P 7/52 | (2006.01) |
| C12P 7/56 | (2006.01) |
| C12P 17/04 | (2006.01) |

(52) U.S. Cl.
CPC ............... *C01F 5/30* (2013.01); *B01D 1/26* (2013.01); *B01D 1/28* (2013.01); *C01B 7/035* (2013.01); *C01F 5/10* (2013.01); *C07C 51/02* (2013.01); *C12P 7/40* (2013.01); *C12P 7/42* (2013.01); *C12P 7/44* (2013.01); *C12P 7/46* (2013.01); *C12P 7/48* (2013.01); *C12P 7/52* (2013.01); *C12P 7/56* (2013.01); *C12P 17/04* (2013.01)

(58) Field of Classification Search
CPC ..... C01F 5/10; C01F 5/30; B01D 1/26; B01D 1/28; C01B 7/035; C07C 51/02; C07C 55/10; C07C 59/08; C07C 59/06; C07C 59/01; C12P 7/40; C12P 7/42; C12P 7/44; C12P 7/46; C12P 7/48; C12P 7/52; C12P 7/56; C12P 17/04
USPC .............. 423/158–161, 164, 178, 639
See application file for complete search history.

(56) References Cited

U.S. PATENT DOCUMENTS

| | | | |
|---|---|---|---|
| 3,980,753 A | 9/1976 | Grill et al. | |
| 10,106,821 B2 * | 10/2018 | De Vries | C12P 7/40 |
| 2014/0335581 A1 * | 11/2014 | De Haan | C12P 7/56 |
| | | | 435/139 |
| 2014/0349355 A1 * | 11/2014 | De Haan | C12P 7/44 |
| | | | 435/142 |

(Continued)

FOREIGN PATENT DOCUMENTS

| | | |
|---|---|---|
| EP | 2666763 A1 * | 11/2013 |
| EP | 2821368 A1 * | 1/2015 |

(Continued)

OTHER PUBLICATIONS

Aug. 3, 2017 International Search Report issued in International Application No. PCT/EP2017/051087.

(Continued)

*Primary Examiner* — Steven J Bos
(74) *Attorney, Agent, or Firm* — Oliff PLC

(57) ABSTRACT

Magnesium chloride solutions including providing aqueous magnesium chloride solution with magnesium chloride concentration of 10-30 wt. % to concentration step where water is evaporated, resulting in concentrated magnesium chloride solution with magnesium chloride concentration of 30-50 wt. %, wherein concentration step is carried out in one or more stages, wherein at least one of the stages is conducted at elevated pressure, withdrawing concentrated magnesium chloride solution from concentration step, and providing it to thermohydrolysis reactor of at least 300° C., withdrawing MgO from thermohydrolysis reactor in solid form, and withdrawing a HCl containing gas stream of at least 300° C. from thermohydrolysis reactor, providing the HCl-containing gas stream of at least 300° C. to cooling step, where HCl-containing gas stream is contacted with cooling liquid, withdrawing HCl-containing gas stream below 150° C. from cooling step, circulating cooling liquid through heat exchanger where energy is transferred to heating liquid which circulates from heat exchanger to concentration step.

30 Claims, 1 Drawing Sheet

(56) References Cited

U.S. PATENT DOCUMENTS

2015/0094491 A1* 4/2015 Kon .................. B01J 39/05
562/580

FOREIGN PATENT DOCUMENTS

| | | |
|---|---|---|
| GB | 1311757 A | 3/1973 |
| WO | 00/017378 A2 | 3/2000 |
| WO | 2013/025106 A1 | 2/2013 |
| WO | 2015/000956 A1 | 1/2015 |

OTHER PUBLICATIONS

Aug. 3, 2017 Written Opinion issued in Patent Application No. PCT/EP2017/051087.

Aug. 11, 2020 Office Action issued in Chinese Patent Application No. 201780006454.1.

"Analysis of Difficult Commodities Classification," Tianjin Customs, China Customs Press, Sep. 30, 2014, 4 pages.

Handbook of Physical and Chemical Constants of chlor-alkali Industry, Beijing Petrochemical Engineering Company, chemical Industry Press, Nov. 30, 1988, 3 pages.

* cited by examiner

METHOD FOR PROCESSING MAGNESIUM CHLORIDE SOLUTIONS AND METHOD FOR MANUFACTURING CARBOXYLIC ACIDS

The present invention pertains to a method for processing magnesium chloride solutions, in particular magnesium chloride solutions derived from the manufacture of organic compounds through fermentation processes. The present invention also pertains to a method for manufacturing carboxylic acids through a fermentation process, in particular a method in which magnesium chloride solutions are generated and processed.

When carboxylic acids are manufactured in a fermentation process a neutralising agent is often added to keep the pH in a range optimal for the microorganism. The neutralising agent is often a base, e.g., an alkaline salt of sodium, potassium, calcium or magnesium. The carboxylic acid will then be present in the fermentation medium in the form of its salt, e.g., a magnesium carboxylate salt.

The magnesium carboxylate salt can be converted to carboxylic acid by reaction with an inorganic acid, e.g. HCl. In this case, the magnesium carboxylate will be converted to carboxylic acid and magnesium chloride, the latter generally in the form of an aqueous solution. After separating the carboxylic acid from the magnesium chloride solution, this solution has to be processed further. One method for processing magnesium chloride solutions is through a thermohydrolysis reaction at elevated temperatures, e.g., above 500° C., where the magnesium chloride reacts with water to yield magnesium oxide and hydrochloric acid.

Methods of this type have been described in literature. For example, WO00/17378 describes a method for manufacturing lactic acid, wherein in a fermentation process a magnesium lactate solution is prepared. The magnesium lactate solution is acidified with HCl to yield a solution comprising lactic acid in a magnesium chloride solution. The lactic acid is recovered from the solution. The resulting magnesium chloride solution may be processed by subjecting it to a thermohydrolysis step at a temperature of at least 500° C. to react the magnesium chloride with water to yield magnesium oxide powder and hydrochloric acid. The heat required for the thermohydrolytic reaction is provided by the in situ combustion of fuel. Traces of organic matter are incinerated.

WO2013/025106 describes a method for manufacturing carboxylic acids through a process comprising the steps of acidifying a magnesium salt of a carboxylic acid with HCl to form an acid and a magnesium chloride solution, and isolating the acid from the solution through precipitation. It is indicated that the magnesium chloride solution may be processed through thermal decomposition.

In WO2015/000956 a method is described for the thermal decomposition of magnesium chloride solutions, in particular solutions derived from the manufacture of carboxylic acid through fermentation. The method encompasses, int.al., the steps of providing an aqueous solution with a MgCl2 concentration of 25-35 wt. % to a preconcentrator where it is contacted with a HCl containing gas stream with a temperature of at least 300° C., providing an aqueous solution with a MgCl2 concentration of 35-45 wt. % resulting from the preconcentrator to a thermohydrolysis reactor, the reactor being at a temperature of at least 300° C., withdrawing MgO from the thermohydrolysis reactor in solid form, and withdrawing a HCl containing gas stream from the thermohydrolysis reactor, said HCl-containing gas stream having a temperature of at least 300° C., providing the HCl-containing gas stream with a temperature of at least 300° C. to the preconcentrator, withdrawing a HCl-containing gas stream with a temperature of at most 150° C. from the preconcentrator.

While this process is attractive from a recycle point of view, and because it allows the separation of organic contaminants, it requires substantial amounts of energy to operate.

There is need in the art for a method for processing magnesium chloride solutions which is more energy-efficient than the method described in WO2015/000956. The present invention provides such a method. The present invention also provides a method for manufacturing carboxylic acids through fermentation encompassing the processing of magnesium chloride solutions.

The present invention pertains to a method for processing magnesium chloride solutions comprising the steps of providing an aqueous magnesium chloride solution with a magnesium chloride concentration of 10-30 wt. % to a concentration step where water is evaporated, resulting in a concentrated magnesium chloride solution with a magnesium chloride concentration of 30-50 wt. %, wherein the concentration step is carried out in one or more stages, wherein at least one of the stages is conducted at elevated pressure, withdrawing the concentrated magnesium chloride solution from the concentration step, and providing it to a thermohydrolysis reactor, the reactor being at a temperature of at least 300° C., withdrawing MgO from the thermohydrolysis reactor in solid form, and withdrawing a HCl containing gas stream having a temperature of at least 300° C. from the thermohydrolysis reactor, providing the HCl-containing gas stream having a temperature of at least 300° C. to a cooling step, where the HCl-containing gas stream is contacted with a cooling liquid, withdrawing a HCl-containing gas stream with a temperature below 150° C. from the cooling step, circulating the cooling liquid through a heat exchanger where energy from the cooling liquid is transferred to a heating liquid which circulates from the heat exchanger to the concentration step.

The present invention also pertains to a method for manufacture of carboxylic acid, comprising the steps of subjecting a carbon source to a fermentation step to form a carboxylic acid, which fermentation step comprises the steps of fermenting a carbon source by means of a microorganism in a fermentation broth to form carboxylic acid and neutralizing at least part of the carboxylic acid by adding a magnesium base selected from magnesium oxide and magnesium hydroxide, thereby obtaining a magnesium carboxylate, subjecting the magnesium carboxylate to an acidification step wherein the magnesium carboxylate is contacted with HCl in an aqueous environment to form an aqueous mixture comprising carboxylic acid and magnesium chloride, subjecting the aqueous mixture comprising carboxylic acid and magnesium chloride to a separation step, to form an effluent comprising carboxylic acid and an aqueous magnesium chloride solution providing an aqueous magnesium chloride solution with a magnesium chloride concentration of 10-30 wt. % to a concentration step where water is evaporated, resulting in a concentrated magnesium chloride solution with a magnesium chloride concentration of 30-50 wt. %, wherein the concentration step is carried out in one or more stages, wherein at least one of the stages is conducted at elevated pressure, withdrawing the concentrated magnesium chloride solution from the concentration step, and providing it to a thermohydrolysis reactor, the reactor being at a temperature of at least 300° C., withdrawing MgO from the thermohydrolysis reactor in solid form, and withdrawing a HCl containing gas stream having a temperature of at least 300° C. from the thermohydrolysis reactor, providing the HCl-containing gas stream having a temperature of at least 300° C. to a cooling step, where the HCl-containing gas stream is contacted with a cooling liquid, withdrawing a HCl-containing gas stream with a temperature below 150° C. from the cooling step, circulating the cooling liquid through a heat exchanger where energy from the cooling liquid is transferred to a heating liquid which circulates from the heat exchanger to the concentration step.

It has been found that the process according to the invention can be operated in a more energy-efficient manner than the process of WO2015/000956. This will be elucidated below.

In the process of WO2015/000956, the evaporation of water in the preconcentrator step takes place in the presence of a HCl-containing gas stream derived from the thermal hydrolysis reactor, which has a temperature of at least 300° C. This is advantageous because the heat present in the HCl-containing gas stream directly helps to drive the evaporation of water in the preconcentrator. However, the presence of HCl places limitations on the operation of the preconcentrator. More specifically, to prevent leakage of HCl to the environment the preconcentrator has to be operated at a pressure which is slightly below atmospheric pressure. The maximum temperature of the magnesium chloride solution is the boiling point at this pressure. The maximum concentration of the magnesium chloride solution therewith is the saturation concentration at this temperature.

In the process of the present invention the steps of concentrating the magnesium chloride solution and cooling of the HCl-containing gas stream are decoupled in that they do not take place in the same unit anymore. This makes it possible to freely select the pressure and temperature in the concentration step.

More specifically, in the method according to the invention, the concentration step is carried out in one or more stages, wherein at least one of the stages is conducted at elevated pressure, therewith increasing the boiling point of the magnesium chloride solution. This in turn increases the saturation concentration of the magnesium chloride solution. This makes it possible to obtain a more concentrated magnesium chloride solution to provide to the thermohydrolysis unit without the risks associated with the presence of solid magnesium chloride particles, e.g., plugging of liquid spray feeders. This results in the evaporation of less water in the thermohydrolysis unit, which makes for a more energy efficient process and the possibility to reduce the scale of its downstream units.

Further advantages of the present invention and specific embodiments thereof will become apparent from the further specification.

The process and its associated advantages will be discussed in more detail below. Reference will be made to the figures, without being limited thereto or thereby.

Figure 1:
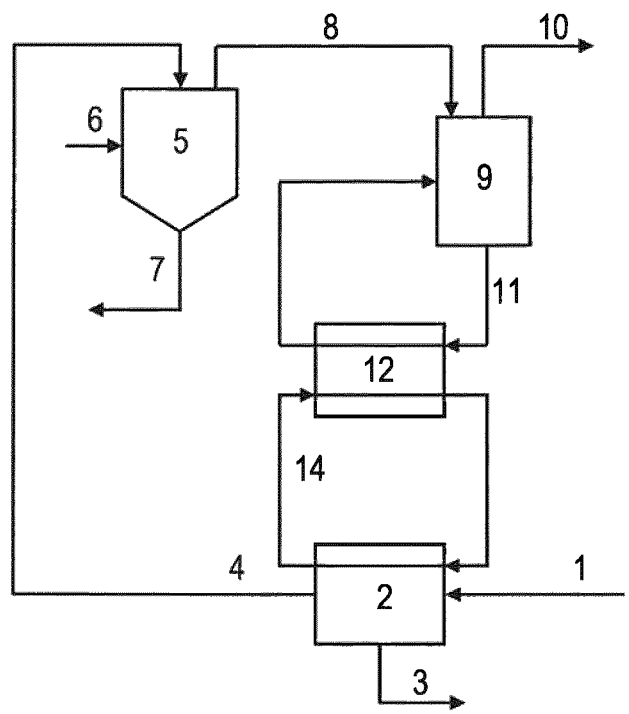
FIG. 1 illustrates the processing of a magnesium chloride solution in accordance with one embodiment of the method according to the invention.

In FIG. 1 a magnesium chloride solution is provided through line 1 to concentrator (2). In concentrator (2), water is evaporated and removed through line (3). A more concentrated magnesium chloride solution is removed from concentrator (2) through line (4), and provided to thermohydrolysis unit (5). The concentration step may be carried out in one or more concentrators (further concentrators not shown). In thermohydrolysis unit (5), the magnesium chloride solution is contacted with hot gas, generally combustion gas, provided through line (6). The magnesium chloride decomposes to form magnesium oxide, which is withdrawn through line (7), and a HCl-containing gas stream with a temperature of at least 300° C., which is withdrawn through line (8). The HCl-containing gas stream is provided to a cooling unit (9), which comprises a cooling liquid. A cooled HCl containing gas stream with a temperature of at most 150° C. is withdrawn from cooling unit (9) through line (10). The cooling liquid is withdrawn from the cooling unit (9) and recirculated through line (11) via heat exchanger (12). Generally a small purge of cooling liquid will be withdrawn from line (11) after the heat exchanger through a line not shown. In heat exchanger (12) heat is transferred from the cooling liquid in line (11) to a heating liquid in line (14). Line (14) is a loop which passes through the heat exchanger (12) and the concentrator (2). It can be seen from FIG. 1 that the process according to the invention thus allows the use of energy generated by the cooling of the HCl-containing gas stream in concentrating the magnesium chloride solution without the HCl-containing gas stream and the magnesium chloride solution being present in the same unit. This makes it possible to independently optimise the evaporation step.

The first step in the process according to the invention is the provision of an aqueous magnesium chloride solution to a concentration step. In the concentration step, the concentration of the magnesium chloride is increased by the evaporation of water. The aqueous magnesium chloride solution provided to the concentration step generally has a magnesium chloride concentration of 10-30 wt. %, in particular 15 to 25 wt. %.

It is a feature of the present invention that the concentration step is carried out in one or more stages, wherein at least one of the stages is conducted at elevated pressure. This increases the boiling point of the magnesium chloride solution, and therewith its saturation concentration. It is preferred for at least one stage in the concentration step to be carried out at a pressure which is at least 1.1 bara. As a maximum, a value of 10 bara may be mentioned. It is considered more preferred to carry out the concentration step at a pressure in the range of 1.1 to 3 bara, in particular 1.5-2.5 bara, specifically 1.5-2 bara. The temperature of the magnesium chloride solution prepared in the concentration step generally is in the range of 100-170° C. It is preferred for the temperature to be at least 120° C., in particular at least 130° C., more in particular at least 140° C., in particular at least 145° C. As indicated above, higher temperatures are attractive because they allow higher magnesium chloride concentrations. On the other hand, if additional energy has to be provided to raise the temperature, this is of course less preferred. It may therefore be preferred for the temperature to be at most 160° C., in particular at most 155° C.

As has been explained above, in the process as described in WO015/000956 it is not possible to carry out the evaporation step at elevated pressure, due to the presence of HCl.

The concentration step in the method according to the invention may be carried out in a single stage or in multiple stages. Where the concentration step is carried out in multiple stages it may be preferred for it to encompass 2-10 concentration stages, in particular 2-6 concentration stages.

In one embodiment, the concentration step is a multiple stage concentration step, wherein steam is withdrawn from a first concentration stage and provided as heating liquid to a further concentration stage. Within this embodiment it is preferred for each concentration stage except the first to be provided with steam from the preceding concentration stage as heating liquid.

In one embodiment, the multiple stage concentration is carried out in a multiple-effect evaporator. A multiple-effect evaporator comprises a set of evaporation vessels wherein each vessel is operated at a pressure which is below the pressure of the preceding vessel. Because the boiling temperature of water decreases as pressure decreases, the vapor boiled off in one vessel can be used to heat the next, and only the first vessel (at the highest pressure) requires an external source of heat. Multiple-effect evaporators are known in the art and require no further elucidation here.

In one embodiment of the present invention, vapor-compression evaporation is used in the concentration step in the process according to the invention, or in one or more stages thereof. In vapour compression evaporation, the vapour produced during evaporation is compressed, e.g., using a blower, compressor or jet ejector, to increase the pressure. Since an increase in pressure results in an increase in condensation temperature, the vapour can be recycled as the heating medium for the solution being concentrated, from which the vapor was generated to begin with. This process is sometimes indicated as vapour compression distillation (VCD). Where the compression is performed by mechanical means, the process is sometimes also indicated as mechanical vapour recompression (MVR). Vapour compression evaporation is known in the art and requires no further elucidation here.

In addition to the reasons given above, the use of multiple-stage concentration may also be preferred in the case that the magnesium chloride solution contains a substantial amount of volatile organic compounds. This can, e.g., be the case if the magnesium chloride solution is derived from a process wherein organic compounds are present, e.g., in the form of extractants. In this case, the use of multiple-stage concentration allows the operation of a first evaporation stage dedicated to the removal of volatile organic components and a relatively limited amount of water, and further evaporation stages to remove the bulk amount of water. In one embodiment, the concentration step in the process according to the invention is a multiple-stage concentration wherein the concentrated product resulting from the first evaporation stage has a total volatile organic compounds (VTOC) content which is at most 50% of the VTOC of the aqueous solution provided to the first evaporation stage, in particular at most 30%, more in particular at most 15%. It is preferred for the concentrated product from the first evaporation stage to have a VTOC of at most 1000 ppm (0.1 wt. %), in particular at most 500 ppm, more in particular at most 200 ppm. Volatile organic compounds are defined in the context of this specification as compounds which are more volatile than water under the conditions of the first evaporation step. The wording "more volatile" means that the percentage of volatile component that is evaporated in the first evaporation stage is larger than the percentage of water that is evaporated in the first evaporation stage.

In the concentration step water is evaporated, resulting in an aqueous magnesium chloride solution which has a magnesium chloride concentration which is higher than that of the starting solution. The concentrated magnesium chloride solution as it is obtained after the concentration step (single stage or multiple stages) generally has a magnesium chloride concentration of 30 to 50 wt. %, in particular 35 to 48 wt. %.

An advantage of the process according to the invention is that relatively high magnesium chloride concentrations can be obtained in this step, which results in less water entering the thermohydrolysis unit. Therefore, it is preferred for the magnesium chloride solution provided to the thermohydrolysis to have a concentration of at least 40 wt. %. A range of 44-47 wt. % may be particularly preferred.

As indicated above, the temperature of this solution can be quite high, e.g., at least 120° C., in particular at least 130° C., more in particular at least 140° C., in particular at least 145° C. As indicated above, at these high temperatures the solution will still be below its saturation concentration, therewith reducing the risk of solid magnesium chloride particles interfering with processing of the solution.

For further information reference is made to what is stated above for the solution prepared in the concentration step (which is the solution provided to the thermohydrolysis unit).

It will be clear to the skilled person that the temperature, pressure, and magnesium chloride concentration of the solution produced in the concentration step and provided to the thermohydrolysis reactor should be selected such that the solution is in the liquid phase and does not contain solid magnesium chloride precipitate which will interfere with further processing. It is within the scope of the skilled person to balance these parameters on the basis of the guidance given in this specification. More in particular, in one embodiment, the solution provided to the thermohydrolysis unit should comprise at most 1 wt. % of solid particles, in particular at most 0.5 wt. %, more in particular at most 0.2 wt. %, still more in particular at most 0.1 wt. %, even more in particular at most 0.05 wt. %, or at most 0.01 wt. %. In one embodiment, the solution provided to the thermohydrolysis unit is substantially free of solid particles.

A gas stream comprising water is withdrawn from the concentration step, and can be processed as desired, e.g., by condensing the water to generate heat.

The aqueous magnesium chloride solution resulting from the concentration step is provided to a thermohydrolysis reactor. In the thermohydrolysis reactor the magnesium chloride reacts with water to form magnesium oxide and HCl.

Suitable apparatuses for conducting the thermohydrolysis step, also indicated herein as thermal decomposition step, are known in the art. For example, a spray roaster or a fluid bed roaster can be used. Such apparatuses can for example be obtained at SMS Siemag, Andritz, Tenova, and CMI Chemline. The use of a spray roaster is preferred. A spray roaster has low energy costs (also compared to a fluid bed roaster), because it requires relatively low temperatures (as described below). A spray roaster was further found to produce reactive MgO particles, which are very suitable for use as a neutralizing agent in fermentation. Thermal decomposition is conducted at a temperature of a least 300° C., which is the minimum temperature at which $MgCl_2$ decomposes. Preferably, thermal decomposition is conducted at a temperature of at least 350° C. Due to energy costs, the temperature is preferably below 1000° C., more preferably below 800° C., still more preferably below 600° C. In addition, using a too high temperature for the thermal decomposition step is undesirable, because it will reduce the reactivity of the MgO formed, such that it is less suitable for use as a neutralizing agent in fermentation. For example, the temperature at which thermal decomposition is conducted may be 350-600° C. or 400-500° C. The temperature mentioned is the temperature of the gases as they are removed from the unit.

Thermal decomposition as applied in the present invention is preferably conducted at a pressure of 0.1-10 bar. However, the use of elevated pressure may be undesirable, because of an increased risk of corrosion in the downstream units due to the HCl not being able to condense. Preferably, thermal decomposition is conducted at atmospheric pressure, in particular when using a roaster, to avoid unnecessary energy costs and the need for expensive high pressure equipment. A pressure in the range of 0.9-1 bar may be preferred to prevent venting of HCl.

From the thermal decomposition step, MgO is withdrawn in solid form. It can be processed as desired. One option for processing this material will be discussed further on.

A HCl containing gas stream with a temperature of at least 300° C. is withdrawn from the thermal decomposition step and provided to a cooling step. In the cooling step the HCl-containing gas stream is contacted with a cooling liquid. The temperature of the HCl-containing gas stream provided to the cooling step is in the range specified above for the temperature during the thermohydrolysis step. The HCl concentration in the gas stream generally is in the range of 5-15 wt. %, in particular 7-12 wt. %. The HCl-containing gas stream generally comprises 20-50 wt. % of water, in particular 30-45 wt. %. Depending on the further composition, the HCl-containing gas stream generally comprises at least 25 wt. % of inert gas, in particular of inert gas selected from the group consisting of $N_2$, $CO_2$ and mixtures thereof (such as air). This may, e.g., result from the thermohydrolysis being conducted in the presence of inert gases, for example in the presence of air. The inert gas concentration may be higher, e.g., at least 50 wt. In one embodiment, the gas feed may comprise 40-80 wt. % nitrogen gas. The gas feed may comprise up to 95 wt. % inert gas. In one embodiment a gas feed obtained in $MgCl_2$ thermohydrolysis is used which comprises 40-50 wt. % $N_2$, 0-5 wt. % $O_2$ and 5-15 wt. % $CO_2$.

A HCl-containing gas stream with a temperature of at most 150° C. is withdrawn from the cooling step. It can be processed as desired, either as a gas stream or after being converted to an aqueous HCl-solution. One option for processing the HCl-containing gas stream will be discussed further on. The HCl-containing gas stream generally has a temperature in the range of 90-150° C., in particular 100-120° C.

For the composition of the HCl containing gas stream withdrawn from the cooling step reference is made to what is stated above for the HCl containing gas stream entering the cooling step.

The cooling liquid used in the cooling step generally is an aqueous liquid. It may be noted that some HCl from the HCl containing gas stream may dissolve in the cooling liquid, resulting in the formation of a HCl solution. Further, the HCl containing gas stream may comprise some magnesium oxide dust, derived from the thermal decomposition step. This will also dissolve in the aqueous liquid. Therewith, even when the process starts out with water as cooling liquid, during the process, the cooling liquid will generally be an acidic magnesium chloride solution. To prevent build-up of magnesium chloride and HCl in the cooling liquid, a small part of the cooling liquid may be purged from the system. Water may be added to compensate for the purge. It is within the scope of the skilled person to address this issue.

The cooling liquid is recycled through a liquid-liquid heat exchanger where energy from the cooling liquid is transferred to a heating liquid which circulates from the heat exchanger to the concentration step. Thus, energy from the hot HCl-containing gas stream is transferred to the cooling liquid in the cooling step, transferred to the heating liquid in the heat exchanger, and finally transferred to the concentration step, where it helps to evaporate water to increase the concentration of the magnesium chloride solution.

Heat exchangers and their operation is known in the art, and require no further elucidation here. It may be preferred for the cooling liquid and the heating liquid to be provided to the heat exchanger in a countercurrent fashion, as this results in an efficient heat transfer due to a large temperature difference. As is part of the common general knowledge of the skilled person, in liquid-liquid heat exchangers, the heating liquid is not in direct contact with the cooling liquid. These liquids are in indirect contact only, as a result of which energy can be transferred from one liquid to another.

The nature of the heating liquid is not critical to the invention. Water is a suitable medium, but other liquids are also possible. It is within the scope of the skilled person to select a suitable liquid.

The temperature of the cooling liquid as it is derived from the cooling step and before it enters the heat exchanger is generally in the range of 90-150° C., in particular 100-120° C. The exact temperature will depend, int. al., on the temperatures at which the HCl containing gas stream enters and leaves the cooling unit and on the boiling point of the cooling liquid. In this context it is noted that the boiling temperature of the cooling liquid may be well above 100° C. due to the presence of dissolved magnesium chloride and HCl.

In the heat exchanger the temperature of the cooling liquid decreases. The temperature of the cooling liquid as it leaves the heat exchanger therewith is at least 2° C., in particular at least 5° C., in some embodiments at least 10° C. below the temperature of the cooling liquid as it enters the heat exchanger. In general, the temperature of the cooling liquid as it exits the heat exchanger is in the range of 80-120° C., depending, int. al., on the temperature of the cooling liquid before the heat exchanger.

As will be evident to the skilled person, as the aim of the heat exchanger is to transfer heat from the cooling liquid to the heating liquid, the temperature of the cooling liquid will be higher than that of the heating liquid at least at one location where the two liquids are in indirect contact.

The heating liquid circulates from the heat exchanger to the concentration step. The temperature of the heating liquid as it enters the heat exchanger is at most the same as the temperature of the cooling liquid as it exits the heat exchanger. In general, the temperature of the heating liquid as it enters the heat exchanger is in the range of 70-95° C. The temperature of the heating liquid as it exits the heat exchanger is at least 2° C., in particular at least 5° C., in some embodiments at least 10° C. above the temperature of the heating liquid as it enters the heat exchanger. In general, the temperature of the heating liquid as it exits the heat exchanger is in the range of 85-115° C.

The heating liquid circulates to the concentrator, where energy is transferred to the magnesium chloride solution to be concentrated. The heating liquid is generally not in direct contact with the magnesium chloride solution in the concentration step. The contact is indirect only, so that energy can be transferred from the heating liquid to the magnesium chloride solution to be evaporated. This can be done in various manners, as will be evident to the skilled person. It can, for example be done by directly circulating the heating liquid through the heating side of the concentrator. It can also be done indirectly by circulating the heating liquid through the heating side of the concentrator, or indirectly, by, e.g., circulating the heating liquid through a (vacuum) flash vessel to form steam, which supplies heat to the concentrator. The embodiment selected depends on whether hot liquid or steam is preferred as the heating element of the concentrator. It is within the scope of the skilled person to select a suitable configuration.

The process according to the invention is particularly suitable for incorporation into a method for manufacturing organic components, in particular carboxylic acids using a fermentation step.

In one embodiment, the invention thus pertains to a method for manufacture of carboxylic acid comprising the steps of subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate, subjecting the magnesium carboxylate to an acidification step wherein the magnesium carboxylate is contacted with HCl in an aqueous environment to form an aqueous mixture comprising carboxylic acid and magnesium chloride, subjecting the aqueous mixture comprising carboxylic acid and magnesium chloride to a separation step, to form an effluent comprising carboxylic acid and an aqueous magnesium chloride solution providing an aqueous magnesium chloride solution with a magnesium chloride concentration of 10-30 wt. % to a concentration step where water is evaporated, resulting in a concentrated magnesium chloride solution with a magnesium chloride concentration of 30-50 wt. %, wherein the concentration step is carried out in one or more stages, wherein at least one of the stages is conducted at elevated pressure, withdrawing the concentrated magnesium chloride solution from the concentration step, and providing it to a thermohydrolysis reactor, the reactor being at a temperature of at least 300° C., withdrawing MgO from the thermohydrolysis reactor in solid form, and withdrawing a HCl containing gas stream having a temperature of at least 300° C. from the thermohydrolysis reactor, providing the HCl-containing gas stream having a temperature of at least 300° C. to a cooling step, where the HCl-containing gas stream is contacted with a cooling liquid, withdrawing a HCl-containing gas stream with a temperature below 150° C. from the cooling step, circulating the cooling liquid through a heat exchanger where energy from the cooling liquid is transferred to a heating liquid which circulates from the heat exchanger to the concentration step.

In a preferred embodiment, the magnesium oxide withdrawn from the thermohydrolysis reactor is recycled at least in part to the fermentation step. This can be done in the form of MgO or after conversion into magnesium hydroxide, e.g., by contacting the magnesium oxide with water to obtain a magnesium hydroxide slurry.

In a preferred embodiment, the HCl-containing gas stream derived from the cooling step is recycled at least in part to the acidification step. In one embodiment the HCl-containing gas stream is converted to a HCl solution by absorbing it in water, and the solution is recycled to the acidification step. In another embodiment, the HCl-containing gas stream is provided to the acidification step in gaseous form.

It is particularly preferred to apply a combination of the MgO recycling and the HCl recycling described above.

The various steps in the integrated process which are additional to the processing of the magnesium chloride solution will be discussed below.

In the first step a carbon source is subjected to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium carboxylate, biomass, and optionally further components such as impurities like are sugars, proteins, and salts.

If so desired, the fermentation broth may be subjected to a biomass removal step, e.g., a filtration step, before further processing. This is generally preferred for improving product quality. Depending on the carboxylic acid produced, another intermediate step may be separation of solid reaction product, e.g., magnesium carboxylate, from the fermentation broth, before, after, or simultaneous with biomass removal, and optionally subjecting the magnesium carboxylate to a washing step.

Depending on the carboxylic acid produced, another intermediate step may be subjecting the fermentation broth to a concentration step to increase the concentration of magnesium carboxylate in the composition before acidification. This step may be carried out before, after, or simultaneous with biomass removal.

Other intermediate steps, e.g., purification steps, may be carried out as desired, as will be evident to the skilled person.

The next step in the integrated process according to the invention is subjecting the magnesium carboxylate to an acidification step, also sometimes indicated as acidification step, wherein the magnesium carboxylate is contacted with HCl in an aqueous environment to form an aqueous mixture comprising carboxylic acid and magnesium chloride.

There are various ways in which this step can be effected. The acidification step is typically conducted by bringing the carboxylate salt in contact with an acidic HCl solution. However, in some embodiments it may also be possible to contact the carboxylate salt with gaseous HCl.

The carboxylate salt may be in solid and/or dissolved form. In one embodiment, the carboxylate salt is provided in solid form. In this case, the acidification step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25%, up to, e.g. 50 wt. %, or e.g. 40 wt. %.

The carboxylate salt may also be in dissolved form, typically as part of an aqueous solution. In this case, the acidification step can be conducted by bringing the carboxylate salt in contact with an acidic solution or an acidic gas.

The acidification step may also be conducted on a mixture of carboxylic acid and carboxylate salt. Such a mixture may for example be obtained in a low pH fermentation. The mixture may for example be an aqueous suspension.

When acidification of the carboxylate salt is conducted by contacting it with an acidic HCl solution, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution. Acidification is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a carboxylate solution or suspension. In particular, HCl gas may be blown through the solution or suspension.

Preferably, acidification is conducted at a temperature of 75° C. or less. At higher temperatures, it becomes uneconomical to adapt equipment to the harsh conditions of an acidic environment at high temperatures.

The acidification step results in the formation of an aqueous liquid comprising carboxylic acid and magnesium chloride. This aqueous liquid is subjected to a separation step, optionally after intermediate processing steps have been carried out such as a concentration step.

Suitable separation steps are known in the art. The nature of the step to be used depends on the nature and properties of the acids.

Where the carboxylic acid is present in whole or in part as solid in the aqueous liquid, separation can take place using conventional solid-liquid separation methods such as filtration, centrifugation, etc.

Where the carboxylic acid is present in whole or in part as a separate organic phase in the aqueous liquid, separation can take place using conventional liquid-liquid separation methods, e.g., decantation, settling, centrifugation, use of plate separators, use of coalescers, and use of hydrocyclones. An extractant may be added to improve the separation efficiency. Combination of different methods and apparatus may also be used.

Where the carboxylic acid is present dissolved in the aqueous liquid, separation can take place using, e.g., extraction with a suitable extractant.

Where an extractant is present in the process according to the invention, the extractant, which may also be indicated as extraction agent is substantially not miscible with water. The use of an extractant results in the formation of a two-phase system during the separation step which comprises a liquid organic layer comprising extraction agent and carboxylic acid and an aqueous layer comprising dissolved magnesium chloride chloride.

Examples of suitable extractants are aliphatic and aromatic hydrocarbons, such as alkanes and aromatic compounds, ketones, and ethers. Mixtures of various compounds may also be used. Examples of suitable aliphatic alkanes are C5-C10 straight chain, branched, or cyclic alkanes, e.g., octane, hexane, cyclohexane, 2-ethyl-hexane, and heptane.

Examples of suitable aromatic compounds are C6-C10 aromatic compounds, e.g., toluene, xylenes, and ethylbenzene.

Examples of suitable ketones are C5+ ketones, more in particular C5-C8 ketones in the present invention. C5+ stands for ketones with at least 5 carbon atoms. The use of C9+ ketones is less preferred. The use of methyl-isobutyl-ketone (MIBK) has been found to be particularly attractive.

Examples of suitable ethers are C3-C6 ethers, e.g., methyl tert-butyl ether (MTBE) and diethyl ether (DEE).

The nature of the carboxylic acid manufactured is not critical to the integrated process according to the invention.

In one embodiment the carboxylic acid is a mono-, di- or tri-carboxylic acid comprising at least 2, but no more than 6 carbon atoms (C2-6 carboxylic acid). In one embodiment, the carboxylic acid is selected from the group consisting of lactic acid, succinic acid, propionic acid, 3-hydroxypropionic acid, 2-, 3-, and 4-hydroxybutyric acid, citric acid, fumaric acid, itaconic acid, adipic acid, acrylic acid, levulinic acid, maleic acid, 2,5-furandicarboxylic acid, mandelic acid, malic acid, and tartartic acid. Preferably, the carboxylic acid is selected from the group consisting of lactic acid, succinic acid, propionic acid, 3-hydroxypropionic acid, 2-, 3-, and 4-hydroxybutyric acid and citric acid.

In one embodiment, the carboxylic acid is selected from the mono-carboxylic acids with 2-6 carbon atoms. In one embodiment, the monocarboxylic acid with 2-6 carbon atoms does not contain hydroxyl-groups. Within this group, examples of suitable acids are propionic acid, acrylic acid, butyric acid, and valeric acid.

In another embodiment, the monocarboxylic acid contains at least one hydroxyl-group. Within this group, in one embodiment it may be preferred to select the acid from the group of lactic acid, glycolic acid, 3-hydroxypropionic acid, 2-, 3-, and 4-hydroxybutyric acid. In another embodiment within this group it may be preferred to select the acid from the group of glycolic acid, 3-hydroxypropionic acid, and 2-, 3-, and 4-hydroxybutyric acid. In a further embodiment it may be preferred for the acid to be lactic acid.

In another embodiment, the carboxylic acid is a polycarboxylic acid, more in particular a di- or tri-carboxylic acid comprising at least 2, but no more than 6 carbon atoms (C2-6 carboxylic acid). In one embodiment, the polycarboxylic acid is selected from the group consisting of succinic acid, citric acid, fumaric acid, itaconic acid, adipic acid, maleic acid, 2,5-furandicarboxylic acid, mandelic acid, malic acid, and tartartic acid. Preferably, the polycarboxylic acid is selected from the group consisting of succinic acid, citric acid, fumaric acid, itaconic acid, adipic acid, and 2,5-furandicarboxylic acid. The polycarboxylic acid may in particular be selected from succinic acid, fumaric acid, itaconic acid, and 2,5-furandicarboxylic acid.

Figure 2:
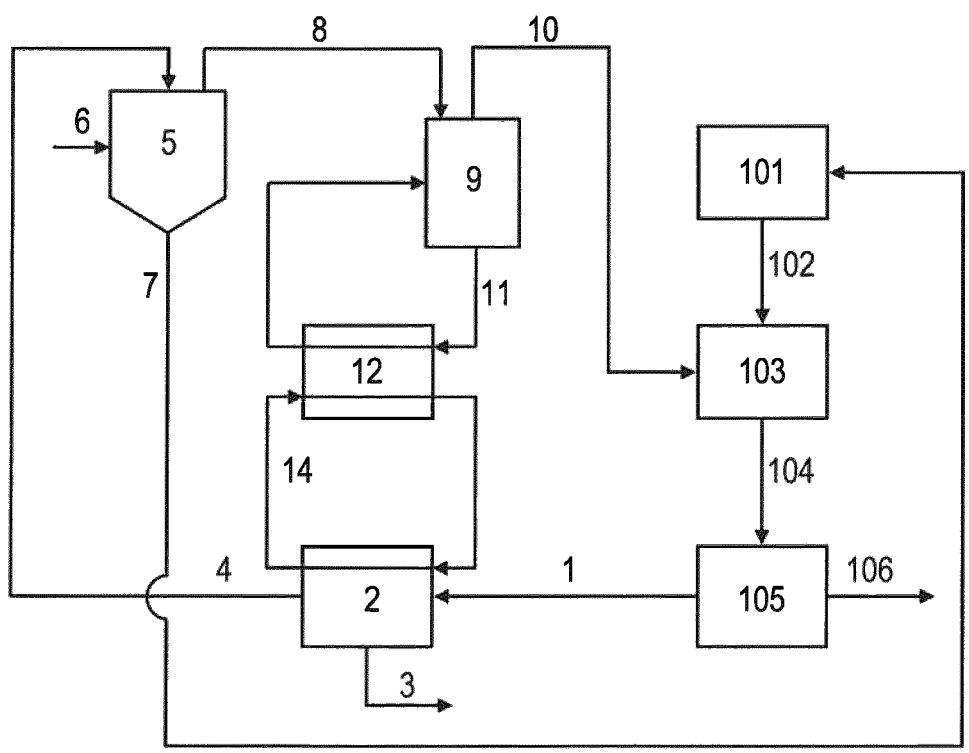
FIG. 2 illustrates a method for manufacturing carboxylic acids according to one embodiment of the present invention.

FIG. 2 illustrates an embodiment of the method according to the invention according to the invention comprising a fermentation step, an acidification step, and recycle of MgO and HCl. In FIG. 2, a fermentation step is carried out in fermentation reactor (101), which is provided with a carbon source and optionally further components such as nutrients through lines not shown. In the fermentation step a carbon source is fermented by means of a micro-organism in a fermentation broth to form carboxylic acid and neutralizing at least part of the carboxylic acid by adding a magnesium base, thereby obtaining a magnesium carboxylate. The magnesium base is added through line (7). The magnesium base is derived from MgO generated in the thermal decomposition step. The MgO may be provided as such, or after having been slurried in an aqueous liquid or converted to magnesium hydroxide in steps not shown.

The fermentation broth comprising a magnesium carboxylate salt is provided to an acidification step (103) through line (102).

Intermediate steps such as biomass removal or concentration may be carried out, but are not shown. In the acidification step (103) the magnesium carboxylate is contacted with HCl in an aqueous environment to form an aqueous mixture comprising carboxylic acid and magnesium chloride. The HCl is provided through line (10) and is derived from the concentrator (2). It may be provided in the form of a HCl-containing gas stream directly derived from preconcentrator (2). It may also be provided in the form of an aqueous solution obtained by absorbing the HCl-containing gas stream into an aqueous liquid (e.g., water). This would take place in an absorption step (not shown).

The aqueous mixture comprising carboxylic acid and magnesium chloride is provided to a separation step (105) through line (104). The separation step may be carried out as described above. Separation step (105) results in an effluent comprising carboxylic acid and a magnesium chloride solution. The product carboxylic acid is withdrawn through line (106). The magnesium chloride solution is withdrawn through line (1), and processed further as described above in the context of FIG. 1).

It will be clear to the skilled person that in the process according to the invention preferred embodiments of various steps can be combined unless they are mutually exclusive.

The invention claimed is:

1. Method for processing magnesium chloride solutions comprising the steps of
    providing an aqueous magnesium chloride solution having a magnesium chloride concentration of 10-30 wt. % to a concentration step where water is evaporated with use of energy from a heating liquid, resulting in a concentrated magnesium chloride solution having a magnesium chloride concentration of 30-50 wt. %, wherein the concentration step is carried out in one or more stages, wherein at least one of the stages is conducted at elevated pressure,
    withdrawing the concentrated magnesium chloride solution from the concentration step, and providing it to a thermohydrolysis reactor, the reactor being at a temperature of at least 300° C.,
    withdrawing MgO from the thermohydrolysis reactor in solid form, and withdrawing a HCl containing gas stream having a temperature of at least 300° C. from the thermohydrolysis reactor,
    providing the HCl-containing gas stream having a temperature of at least 300° C. to a cooling step, where the HCl-containing gas stream is contacted with a cooling liquid,
    withdrawing a HCl-containing gas stream having a temperature below 150° C. from the cooling step,
    circulating the cooling liquid through a heat exchanger where energy from the cooling liquid is transferred to the heating liquid, which heating liquid then circulates from the heat exchanger to provide the energy to the concentration step.

2. Method according to claim 1, wherein the concentration step is carried out in one or more stages, wherein at least one of the stages is conducted at a pressure of at least 1.1 bara and at most 10 bara.

3. Method according to claim 1 wherein the concentration step is carried out in multiple stages.

4. Method according to claim 3 wherein steam is withdrawn from a first concentration stage and provided as heating liquid to a further concentration stage.

5. Method according to claim 3 wherein the multiple stage concentration is carried out in a multiple-effect evaporator.

6. Method according to claim 1 wherein vapor-compression evaporation is used in the concentration step.

7. Method according to claim 1 wherein the magnesium chloride solution provided to the thermohydrolysis reactor has a concentration of 30-48 wt. % and a temperature of 100-170° C.

8. Method according to claim 1, wherein a temperature of the cooling liquid leaving the cooling step and before entering the heat exchanger is in the range of 90–150° C.

9. Method according to claim 1 wherein a temperature of the cooling liquid leaving the heat exchanger is at least 2° C. below the temperature of the cooling liquid entering the heat exchanger.

10. Method according to claim 1 wherein a temperature of the heating liquid entering the heat exchanger is in the range of 70–95° C.

11. Method according to claim 1 wherein a temperature of the heating liquid exiting the heat exchanger is at least 2° C. above the temperature of the heating liquid entering the heat exchanger.

12. Method according to claim 1 wherein the energy from the heating liquid is indirectly provided to the concentration step by circulating the heating liquid from the heat exchanger through a flash vessel, and the flash vessel supplies steam to at least one stage of the concentration step.

13. Method according to claim 7, wherein the magnesium chloride solution provided to the thermohydrolysis reactor has a concentration of 35-48 wt. %.

14. Method according to claim 13, wherein the magnesium chloride solution provided to the thermohydrolysis reactor has a concentration of 40-48 wt. %.

15. Method according to claim 14, wherein the magnesium chloride solution provided to the thermohydrolysis reactor has a concentration of 45-48 wt. %.

16. Method according to claim 7, wherein the magnesium chloride solution provided to the thermohydrolysis reactor has a temperature of 120-170° C.

17. Method according to claim 16, wherein the magnesium chloride solution provided to the thermohydrolysis reactor has a temperature of 130-170° C.

18. Method according to claim 17, wherein the magnesium chloride solution provided to the thermohydrolysis reactor has a temperature of 140-170° C.

19. Method according to claim 18, wherein the magnesium chloride solution provided to the thermohydrolysis reactor has a temperature of 145-170° C.

20. Method according to claim 9, wherein the temperature of the cooling liquid leaving the heat exchanger is at least 5° C. below the temperature of the cooling liquid entering the heat exchanger.

21. Method according to claim 20, wherein the temperature of the cooling liquid leaving the heat exchanger is at least 10° C. below the temperature of the cooling liquid entering the heat exchanger.

22. Method according to claim 11, wherein the temperature of the heating liquid exiting the heat exchanger is at least 5° C. above the temperature of the heating liquid entering the heat exchanger.

23. Method according to claim 22, wherein the temperature of the heating liquid exiting the heat exchanger is at least 10° C. above the temperature of the heating liquid entering the heat exchanger.

24. Method for manufacture of carboxylic acid comprising the steps of
subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from the group consisting of magnesium oxide, magnesium hydroxide, and a combination thereof, thereby obtaining a magnesium carboxylate,
subjecting the magnesium carboxylate to an acidification step wherein the magnesium carboxylate is contacted with HCl in an aqueous environment to form an aqueous mixture comprising carboxylic acid and magnesium chloride,
subjecting the aqueous mixture comprising carboxylic acid and magnesium chloride to a separation step, to form an effluent comprising carboxylic acid and an aqueous magnesium chloride solution,
providing the aqueous magnesium chloride solution, having a magnesium chloride concentration of 10-30 wt. % to a concentration step where water is evaporated with use of energy from a heating liquid, resulting in a concentrated magnesium chloride solution having a magnesium chloride concentration of 30-50 wt. %, wherein the concentration step is carried out in one or more stages, wherein at least one of the stages is conducted at elevated pressure,
withdrawing the concentrated magnesium chloride solution from the concentration step, and providing it to a thermohydrolysis reactor, the reactor being at a temperature of at least 300° C.,
withdrawing MgO from the thermohydrolysis reactor in solid form, and withdrawing a HCl containing gas stream having a temperature of at least 300° C. from the thermohydrolysis reactor,
providing the HCl-containing gas stream having a temperature of at least 300° C. to a cooling step, where the HCl-containing gas stream is contacted with a cooling liquid,
withdrawing a HCl-containing gas stream having a temperature below 150° C. from the cooling step,
circulating the cooling liquid through a heat exchanger where energy from the cooling liquid is transferred to the heating liquid, which heating liquid then circulates from the heat exchanger to provide the energy to the concentration step.

25. Method according to claim 24 comprising the further steps of
recycling the magnesium oxide withdrawn from the thermohydrolysis reactor at least in part to the fermentation step,
recycling the HCl-containing gas stream derived from the cooling step at least in part to the acidification step, or
recycling the magnesium oxide withdrawn from the thermohydrolysis reactor at least in part to the fermentation step and recycling the HCl-containing gas stream derived from the cooling step at least in part to the acidification step.

26. Method according to claim 25, wherein the recycling the magnesium oxide withdrawn from the thermohydrolysis reactor comprises converting the magnesium oxide into magnesium hydroxide.

27. Method according to claim 24, wherein the aqueous mixture comprising carboxylic acid and magnesium chloride is separated using (1) filtration and/or centrifugation, (2) using decantation, settling, centrifugation, a plate separator, a coalescer and/or a hydrocyclone, or (3) using extraction with an extractant.

28. Method according to claim 24, wherein the carboxylic acid is a mono-, di- or tri-carboxylic acid comprising 2 to 6 carbon atoms.

29. Method according to claim 28, wherein the carboxylic acid is selected from the group consisting of lactic acid, succinic acid, propionic acid, 3-hydroxypropionic acid, 2-hydroxybutyric acid, 3-hydroxybutyric acid, 4-hydroxybutyric acid, citric acid, fumaric acid, itaconic acid, adipic acid, acrylic acid, levulinic acid, maleic acid, 2,5-difurandicarboxylic acid, mandelic acid, malic acid, and tartaric acid.

30. Method according to claim 29, wherein the carboxylic acid is lactic acid.

* * * * *